United States Patent
Sunohara et al.

(10) Patent No.: US 7,094,348 B2
(45) Date of Patent: Aug. 22, 2006

(54) DIALYZER AND METHOD FOR MANUFACTURING THE SAME

(75) Inventors: Takashi Sunohara, Osaka (JP); Akinobu Yamaguchi, Osaka (JP)

(73) Assignee: Nipro Corporation, Osaka (JP)

( * ) Notice: Subject to any disclaimer, the term of this patent is extended or adjusted under 35 U.S.C. 154(b) by 100 days.

(21) Appl. No.: 10/387,493

(22) Filed: Mar. 14, 2003

(65) Prior Publication Data
US 2003/0196949 A1 Oct. 23, 2003

(30) Foreign Application Priority Data
Mar. 14, 2002 (JP) .............................. 2002-069870

(51) Int. Cl.
*B01D 63/02* (2006.01)
*C02F 1/44* (2006.01)

(52) U.S. Cl. .................. 210/321.88; 210/321.79; 210/500.23; 210/321.71; 210/321.61

(58) Field of Classification Search ............ 210/321.6, 210/321.61, 321.72, 321.79, 321.8, 321.81, 210/321.71
See application file for complete search history.

(56) References Cited

U.S. PATENT DOCUMENTS 4,219,426 A * 8/1980 Spekle et al. ............... 210/232

FOREIGN PATENT DOCUMENTS

| EP | 0 701 826 A2 | 3/1996 |
|---|---|---|
| FR | 2 267 138 | 11/1975 |
| JP | 08-168525 A | 7/1996 |
| JP | 08-192031 A | 7/1996 |
| JP | 11-000394 A | 1/1999 |
| JP | 11-009684 A | 1/1999 |
| JP | 2961481 B2 | 8/1999 |
| JP | 11-319079 A | 11/1999 |
| JP | 11-319080 A | 11/1999 |
| WO | 98/22161 A1 | 5/1998 |

OTHER PUBLICATIONS

English translation copy of French Patent No. 2,267,138.*
Schmidt, M., et al.; "Backfiltration in Hemodialyzers with Highly Permeable Membranes: An in vitro and in vivo Investigation"; *Blood Purification 2*; pp. 108-114; 1984.
Gejyo, Fumitake, et al.; "β2-microglobulin: A new form of amyloid protein associated with chronic hemodialysis"; *Kidney International*; vol. 30, pp. 385-390; 1986.
Dellanna, F., et al.; "Internal filtration—advantage in haemodialysis?"; *Nephrol Dial Transplant 11, Suppl. 2*; pp. 83-86; 1996.

* cited by examiner

Primary Examiner—Krishnan S. Menon
(74) Attorney, Agent, or Firm—Kubovcik & Kubovcik (57) ABSTRACT

A dialyzer in which a nearly cylindrical case is provided therein with a hollow fiber bundle made of a plurality of hollow fiber membranes, a blood flow path formed by lumens of the hollow fiber membranes, a dialyzate flow path formed by a space between the inner wall of the case and the hollow fiber membranes and a cylindrical heat-shrinkable tube provided on the outside of the hollow fiber bundle and at least a part of which can be shrunk by heating, and a method for manufacturing the dialyzer.

3 Claims, 9 Drawing Sheets

DIALYZER AND METHOD FOR MANUFACTURING THE SAME

BACKGROUND OF THE INVENTION

The present invention relates to a dialyzer used in dialysis. More specifically, it relates to an internal filtration accelerating-type dialyzer which can increase an internal filtration rate and an internal backfiltration rate within the dialyzer.

For therapy of patients whose renal function is impaired, for example, patients whose function of removing waste products or the like in blood is impaired because of renal insufficiency or the like, therapy by blood purification such as hemodialysis or hemodialytic filtration has so far been performed. In this blood purification therapy, urea, creatinine, uric acid, low-molecular proteins, water and the like accumulated in blood are removed by bringing the blood into contact with a dialyzate through semipermeable membranes in a dialyzer.

In recent years, a substance that causes amyloidosis, which is one of complications in dialysis, has been identified as $\beta_2$ microglobulin having a molecular weight of 11,800 (F. Gejyo et al., Kidney International, vol.30, pp. 385–390, 1986). Since $\beta_2$ microglobulin having a high molecular weight has a low diffusion rate, removal efficiency is higher by hemofiltration than by hemodialysis. Further, since a substance having a low molecular weight, such as urea, has a high diffusion rate, removal efficiency is higher by hemodialysis than by hemofiltration. Accordingly, a hemodialytic filtration therapy (HDF) being a combination of hemodialysis and hemofiltration has been conceived. In the HDF therapy, filtration of a large amount of fluid is conducted with a dialyzer and a replenisher is supplied in a blood circuit. Therefore, an exclusive device with a complicated structure is required.

Meanwhile, a dialyzer excellent in product permeability and water permeability, which can remove $\beta_2$ microglobulin having a high molecular weight, has been developed. It has been found that such a dialyzer excellent in product permeability and water permeability allows filtration and backfiltration between a blood and a dialyzate via a semipermeable membrane (hereinafter referred to as internal filtration and internal backfiltration) even when forced filtration by dewatering is not performed (M. Schmidt et al., Blood Purification 2: 108–114,1984). Accordingly, a hemodialytic filtration method that performs filtration and replenishment by increasing an amount of internal filtration and an amount of internal backfiltration has been proposed. Additionally, an internal filtration accelerating-type dialyzer capable of increasing dialysis efficiency, which is used in the hemodialytic filtration method, is being developed.

Usually, the internal filtration and the internal backfiltration do not occur at a same position within a dialyzer. Since blood and a dialyzate are passed through a dialyzer in directions opposite to each other, a fluid having a higher pressure moves to a fluid having a lower pressure via a semipermeable membrane regarding the blood and the dialyzate. That is, there is a tendency that the internal filtration occurs on a blood inflow side within a dialyzer and the internal backfiltration occurs on a blood outflow side within a dialyzer.

For increasing an internal filtration rate and an internal backfiltration rate in a dialyzer, it is necessary to increase a pressure loss along a blood flow path or a dialyzate flow path. The pressure loss along the flow path is represented by the Hagen-Posuille formula which is a pressure loss inducing formula of laminar flow in a cylindrical tube.

$$\Delta P = 8 \mu L Q / \pi R^4$$

($\Delta P$: pressure loss of a flow path [Pa],
$\mu$: viscosity of a fluid [Pa·s],
L: length of a flow path [m],
R: radius of a flow path [m],
Q: volume flow rate [m$^3$/s])

It is found that to increase the pressure loss $\Delta P$ along the flow path, the volume flow rate Q may be increased, the sectional area of the flow path $\pi R^2$ may be decreased or the length L of the flow path may be increased.

For increasing an internal filtration rate and an internal backfiltration rate of a dialyzer, a dialyzer, the length of the flow path of which is increased by increasing a total length, (Japanese Patent No. 2961481) and a dialyzer, a sectional area of a blood flow path of which is decreased by decreasing an inner diameter of a hollow fiber membrane, (F. Dellanna et al., Nephrol Dial Transplant 11, Suppl. 2: 83–86, 1996) have so far been known.

However, in the dialyzer with the total length increased, for obtaining effects of sufficient acceleration of internal filtration and internal backfiltration, the length of the flow path has to be increased to more than twice the length of the flow path in an ordinary dialyzer. Such a dialyzer is impractical. Further, in the dialyzer with the inner diameter of the hollow fiber membrane decreased, there is a likelihood that irregularity occurs in the inner diameter of the hollow fiber membrane during manufacture or blood remaining in lumens of the hollow fiber membranes after use of the dialyzer is increased.

Further, there has been proposed as a dialyzer, a cross-sectional area of a dialyzate flow path of which is decreased by increasing a packing ratio of hollow fiber membranes, a dialyzer, a hollow fiber bundle of which is shrunk with a net or the like (Japanese Patent Laid-Open No. 168525/1996 and Domestic Republication WO 98/22161). However, in the dialyzer with the hollow fiber bundle shrunk, the diameter of the hollow fiber bundle has to be decreased more than necessary for inserting the hollow fiber bundle into a case. Therefore, the hollow fiber membranes might be ruptured and the packing ratio of the hollow fiber membranes inserted into the case is not high enough.

Moreover, as a dialyzer with a decreased sectional area of a dialyzate flow path, a dialyzer in which a bonded mat having a property of being swelled with a dialyzate is introduced in a dialyzate, flow path (Japanese Patent Laid-Open Nos. 192031/1996 and 9684/1999, Domestic Republication WO 98/22161), a dialyzer in which a bag-shaped member is introduced into a dialyzate flow path and the bag-shaped member is swelled by introducing therein a physiological saline or the like at the time of using the dialyzer (Japanese Patent Laid-Open Nos. 394/1999 and 319080/1999, Domestic Republication WO 98/22161), a dialyzer in which a sectional area of a dialyzate flow path is capable of changing by changing the case of the dialyzer with pressure applied from outside the case (Japanese Patent Laid-Open No. 319079/1999) and the like have also been developed.

In a dialyzer in which a bonded mat having a property of being swelled with a dialyzate is introduced, the bonded mat has itself a thickness so that an amount of the product that can be introduced into the dialyzer is limited. When the amount of the bonded mat is large, it is difficult to insert the hollow fiber bundle into the case of the dialyzer. Meanwhile, when the amount of the bonded mat is small, the sectional area of the dialyzate flow path is not sufficiently lowered. Further, in a dialyzer with the bonded mat having the swelling property introduced being wound, the hollow fiber bundle is previously inserted into the lumen of the product having a far smaller inner diameter than the inner diameter of the case and then inserted into the case so that the hollow fiber membranes might be ruptured.

On the other hand, in a dialyzer in which a bag-shaped member is swelled, the structure is complicated and a force exerted in swelling the bag-shaped member is also exerted on the case of the dialyzer. Thus, improvement in the case material is required for the case to have a satisfactory rigidity. Further, in a dialyzer, the sectional area of the dialyzate flow path of which is capable of changing by changing the case thereof, a part of the case is changed by pressure applied from outside of the case. With such a dialyzer, pressure has to be continued to be applied during changing of the sectional area of the dialyzate flow path so that the structure of the dialyzer is more complicated.

SUMMARY OF THE INVENTION

Under these circumstances, an object of the invention is to provide a dialyzer which can solve the foregoing problems associated with conventional dialyzers. More specifically, an object of the invention is to provide a dialyzer which is simple in structure without fear of rupturing hollow fiber membranes during fabrication and in which an internal filtration rate and an internal backfiltration rate are increased by decreasing a sectional area of the dialyzate flow path.

The present inventors have assiduously conducted investigations and have consequently found that a dialyzer, which is provided with a heat-shrinkable tube, at least a part of which can be shrunk by heating, on an outside of a hollow fiber bundle inserted in the dialyzer, can solve the foregoing problems.

That is, the invention is a dialyzer in which a nearly cylindrical case is provided therein with a hollow fiber bundle made of a plurality of hollow fiber membranes, a blood flow path formed by lumens of the hollow fiber membranes, a dialyzate flow path formed by gaps between the hollow fiber membranes and a gap between the inner wall of the case and the hollow fiber membranes, and a cylindrical heat-shrinkable tube provided on an outside of the hollow fiber bundle and at least a part of which can be shrunk by heating, and a method for manufacturing the dialyzer.

DESCRIPTION OF THE DRAWINGS

The dialyzer of the present invention is described in detail below by referring to preferable embodiments shown in the appended drawings. However, the present invention is not limited to these embodiments.

FIGS. 7 (7a–c) is a diagrammatic view of a method for manufacturing the dialyzer of the present invention.

FIG. 8(a–d) is a diagrammatic view of another method for manufacturing the dialyzer of the present invention.

DETAILED DESCRIPTION OF THE INVENTION

Figure 1:
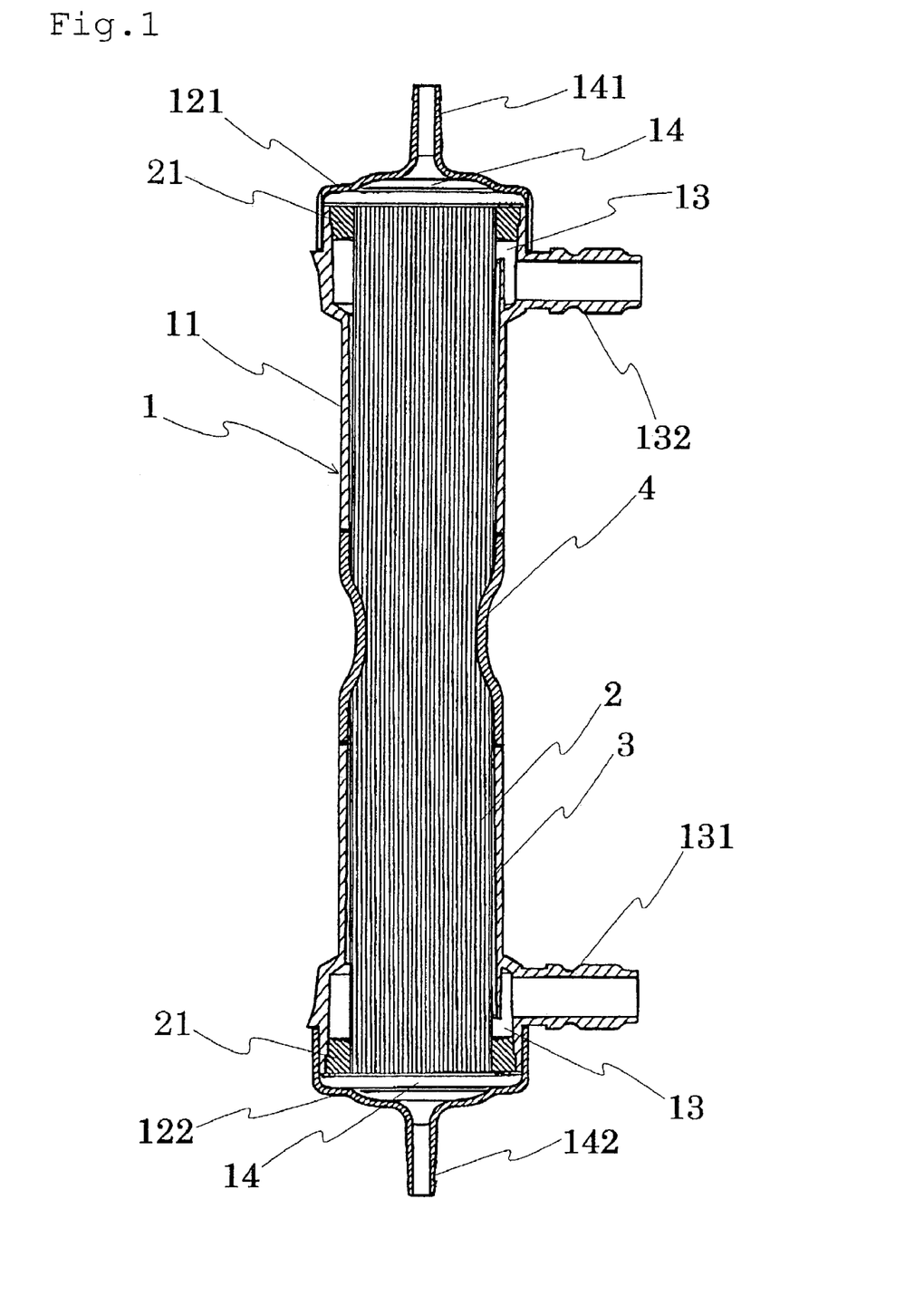
FIG. 1 is a longitudinal sectional view showing an embodiment of the dialyzer of the present invention before use.

As shown in FIG. 1, the dialyzer, an example of the present invention, is comprised of a nearly cylindrical case (or container) 1 with both ends open, a hollow fiber bundle 3 made of a plurality of hollow fiber membranes 2 and inserted into the cylindrical case 1 and a cylindrical heat-shrinkable tube 4 provided on an outside of the hollow fiber bundle 3 and at least a part of which can be shrunk by heating.

The case 1 in the dialyzer of the present invention has a nearly cylindrical case body 11 with both ends open and caps 121 and 122 mounted on both ends of the case body 11. The case body 11 is further provided with a dialyzate inlet 131 and a dialyzate outlet 132. The cap 121 is provided with a blood inlet 141 and the cap 122 is provided with a blood outlet 142.

The case body 11 and the caps 121 and 122 are made of a hard resin such as, for example, polyethylene, polypropylene, polycarbonate, acrylic resin such as polymethyl methacrylate, hard polyvinyl chloride, styrene-butadiene copolymer or polystyrene. For providing blood visibility inside the dialyzer, the material constituting the case body 11 and the caps 121 and 122 is preferably transparent or semitransparent. For discriminating between the blood inlet 141 and the blood outlet 142, the caps 121 and 122 may be formed of materials colored in different tints.

The hollow fiber bundle 3 made of a plurality of hollow fiber membranes 2 is accommodated in the case 1. With respect to the hollow fiber membrane 2, a membrane made of a material relatively excellent in heat resistance, such as polysulfone, polyether sulfone, polyacrylonitrile, polyamide, polyethylene or polypropylene is preferably used. It is preferable that an ultrafiltration rate (UFR) of the hollow fiber membrane 2 is 20 mL/hr·m²·mmHg or more in order to surely remove unnecessary ingredients in a blood.

The hollow fiber membranes 2 are accommodated in the case 1 in a state of a hollow fiber bundle 3 obtained by bundling from 100 to 12,000 membranes. The effective membrane area of the hollow fiber membranes 2 in the dialyzer is preferably from 0.1 to 3.0 m², more preferably from 0.1 to 2.5 m². Further, the packing ratio of the hollow fiber membranes 2 in the case 1 is preferably from 20 to 80%, more preferably from 40 to 60%.

The hollow fiber bundle 3 is fixed in the case 1 by injecting a potting agent 21 in a space between the inner wall of the case body 11 and the hollow fiber membranes 2 on both ends of the hollow fiber bundle 3 and curing it, without clogging the lumens of the hollow fiber membranes 2. As the potting agent 21, polyurethane, silicone, epoxy resin or the like is preferably used. The potting agent 21 closes a dialyzate flow path 13 to be described later on both ends of the hollow fiber membranes 2 in order to prevent the dialyzate passing through the dialyzate flow path 13 from flowing into the blood inlet 141 and the blood outlet 142 on both ends of the hollow fiber membranes 2.

In the dialyzer of the present invention, the hollow fiber bundle 3 is accommodated in the case 1 to provide the dialyzate flow path 13 formed by gaps between the hollow fiber membranes and between the inner wall of the case 1 and the hollow fiber membranes 2 and a blood flow path 14 formed by the lumens of the hollow fiber membranes. One end of the dialyzate flow path 13 communicates with the dialyzate inlet 131, and another end communicates with the dialyzate outlet 132. Further, one end of the blood flow path 14 communicates with the blood inlet 141, and another end communicates with the blood outlet 142. When the dialyzer is used, blood flows from the blood inlet 141 to the blood outlet 142 via the blood flow path 14, and the dialyzate flows from the dialyzate inlet 131 to the dialyzate outlet 132 via the dialyzate flow path 13. The dialysis can be performed at good efficiency by flowing the blood and the dialyzate in opposite directions through the hollow fiber membranes 2.

When a constricted portion is formed between the dialyzate inlet 131 and the dialyzate outlet 132 on the case body 11 of the dialyzer, the sectional area of the dialyzate flow path 13 is decreased and a pressure loss of the dialyzate is increased. As a result, internal filtration and internal backfiltration are accelerated. Therefore, the case body 11 in the dialyzer of the present invention may have a constricted portion unless the insertion of the hollow fiber bundle 3 into the case 1 is hindered.

In the dialyzer of the present invention, the cylindrical heat-shrinkable tube 4 is mounted in the space between the inner wall of the case body 11 and the outer surface of hollow fiber bundle 3. The heat-shrinkable tube 4 is formed of a material which is shrunk by heating, for example, a polyfluoroethylene-type fiber such as PTFE, FEP, TFE or PFA, polyethylene, polypropylene, polyester, vinyl chloride, synthetic rubber or silicone rubber. More preferably, the tube 4 is formed of a transparent or semitransparent material. The heat-shrinkable tube 4 of the present invention may be wholly formed of the foregoing material, or a portion to be shrunk may be formed of the foregoing material and other portions may be formed of a non-heat-shrinkable material such as polycarbonate or acrylic resin.

Figure 2:
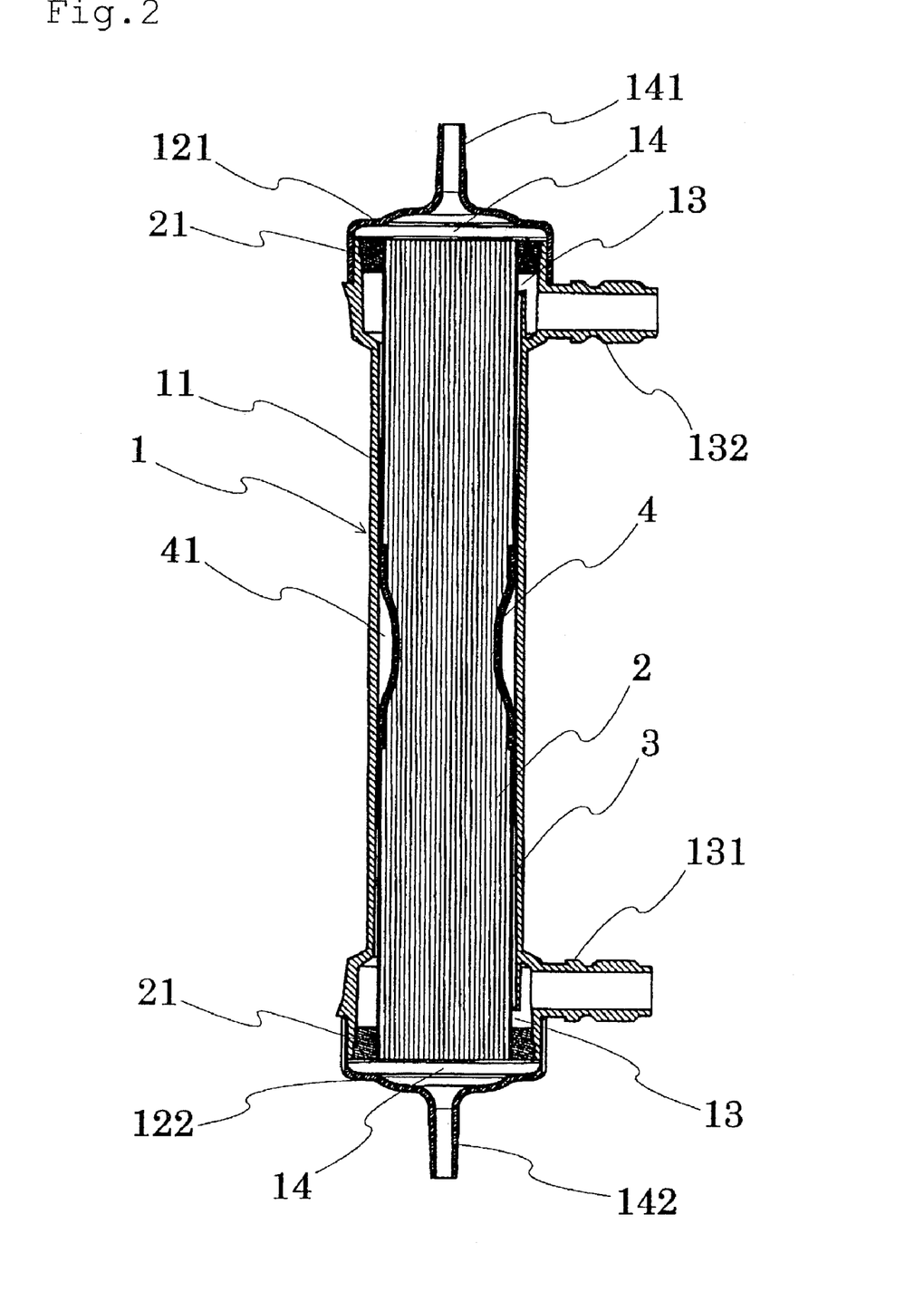
FIG. 2 is a longitudinal sectional view showing another embodiment of the dialyzer of the present invention.

The heat-shrinkable tube 4 may be combined in the case 1 as shown in FIG. 1, or may be fixed to the inner wall of the case 1 as shown in FIG. 2. In the dialyzer in which the heat-shrinkable tube 4 is combined in the case 1 shown in FIG. 1, a part of the case body 11 may be formed of the heat-shrinkable tube 4 or the whole of the case body 11 may be formed of the heat-shrinkable tube 4. With respect to the dialyzer in which a part of the case body 11 is formed of the heat-shrinkable tube 4, the case body 11 is formed by insert molding, ultrasonic fusion or solvent bonding.

In the dialyzer in which the heat-shrinkable tube 4 is fixed to the inner wall of the case 1, an outer diameter of the heat-shrinkable tube 4 before being shrunk is preferably of such a size that the tube 4 is easily inserted into the case 1 and water-tightly contacted with the inner wall of the case body 11. Further, an inner diameter of the heat-shrinkable tube 4 before being shrunk is of such a size that a packing ratio of the hollow fiber bundle 3 in a portion in which the tube 4 is inserted in the case body 11 is preferably from 30 to 60%, more preferably from 40 to 50%. A thickness of the heat-shrinkable tube 4 is properly determined according to its material and is preferably from 0.1 to 2 mm, more preferably from 0.2 to 1.0 mm. Accordingly, it is possible with the dialyzer of the present invention to easily insert the hollow fiber bundle 3 into the case 1.

Figure 3:
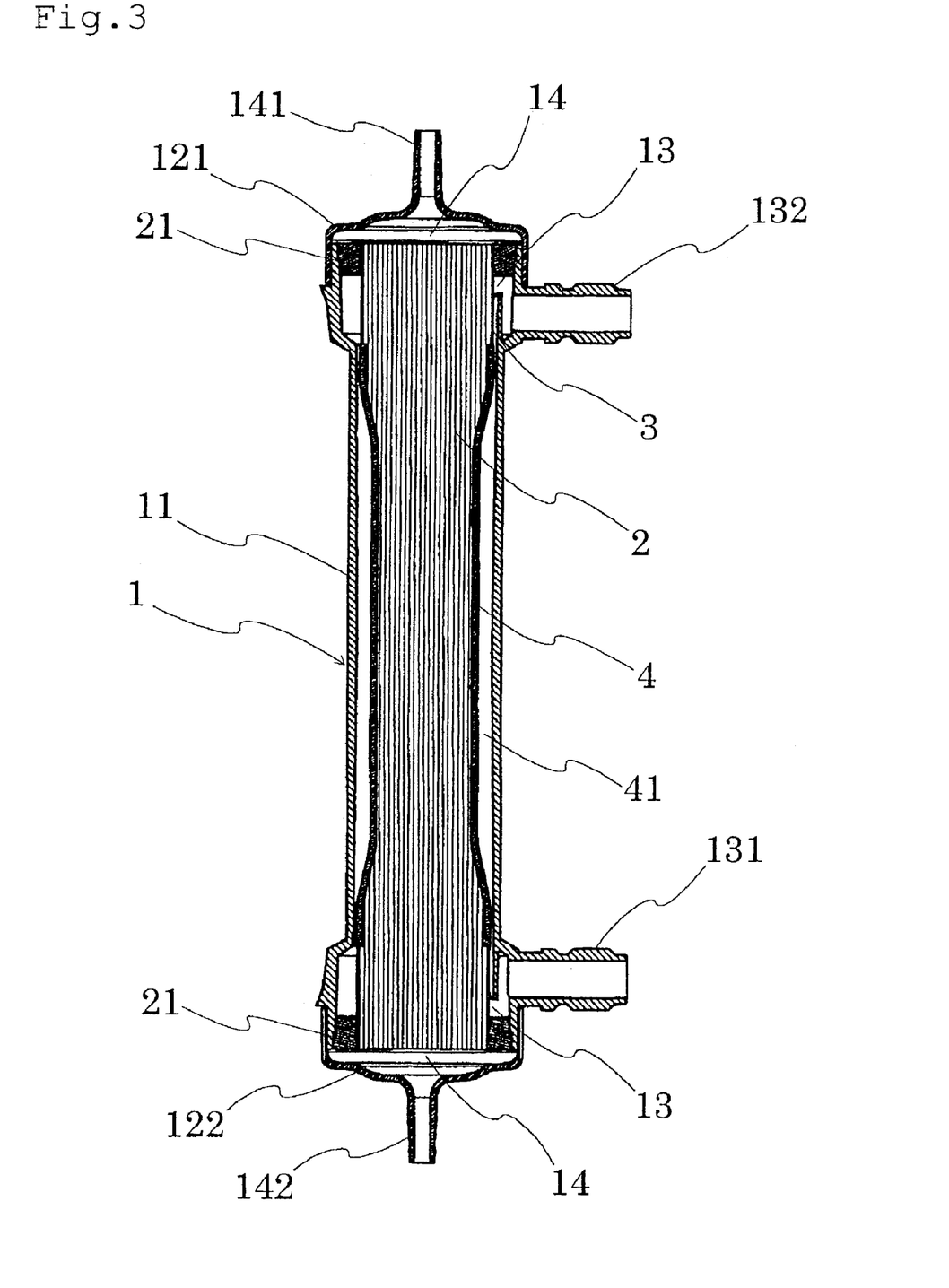
FIG. 3 is a longitudinal sectional view showing another embodiment of the dialyzer of the present invention.

A total length of the heat-shrinkable tube 4 before being shrunk is properly changed within a length which is less than a length from the dialyzate inlet 131 to the dialyzate outlet 132 in the case body 11. As shown in FIG. 2, when the heat-shrinkable tube 4 is short, the material cost is low and the heat-shrinking time of the dialyzer is short. Further, as shown in FIG. 3, when the heat-shrinkable tube 4 is long, the internal filtration and the internal backfiltration of a sufficient amount of fluid can be performed even when using a material having a low heat shrinkage percentage.

The heating of the heat-shrinkable tube 4 is conducted preferably with a heating device made of brass or a drier, or by infrared irradiation, far-infrared irradiation or the like. For example, the heat-shrinkable tube is heated and shrunk by being compressed with a heating device made of brass which is a tubular device having a c-shaped cross-section that is heated at about 90 to 120° C. The heat-shrinkable tube 4 preferably has a property of being shrunk by heating at from 40 to 120° C., more preferably from 40 to 100° C., which does not influence or affect the hollow fiber membranes 2.

In the heat-shrinkable tube 4 after being shrunk, the packing ratio of the hollow fiber bundle 3 in the shrunk portion of the heat-shrinkable tube 4 is from 70 to 90%, preferably from 75 to 80%. The shrinkage percentage of the heat-shrinkable tube 4 can be adjusted by changing the heating temperature, the material and thickness.

The shrinking of the heat-shrinkable tube 4 is conducted for the purpose of decreasing the sectional area of the dialyzate flow path 13. In the dialyzer shown in FIG. 2, when the heat-shrinkable tube 4 is shrunk, a space 41 is sometimes formed between the inner wall of the case body 11 and the heat-shrinkable tube 4. When the space 41 communicates with the dialyzate flow path 13, the dialyzate passing through the dialyzate flow path 13 flows into the space 41. Thus, the original purpose of decreasing the sectional area of the dialyzate flow path 13 is not attained. Accordingly, in order to prevent the dialyzate from flowing into the space 41, it is preferred that the central portion of the heat-shrinkable tube 4 is locally heated and shrunk as shown in FIG. 2. The heated central portion of the heat-shrinkable tube 4 shrinks to decrease the sectional area of the dialyzate flow path 13, while the unheated ends of the heat-shrinkable tube 4 do not shrink, which makes it possible to prevent the dialyzate passing through the dialyzate flow path 13 from entering the space 41.

Figure 4:
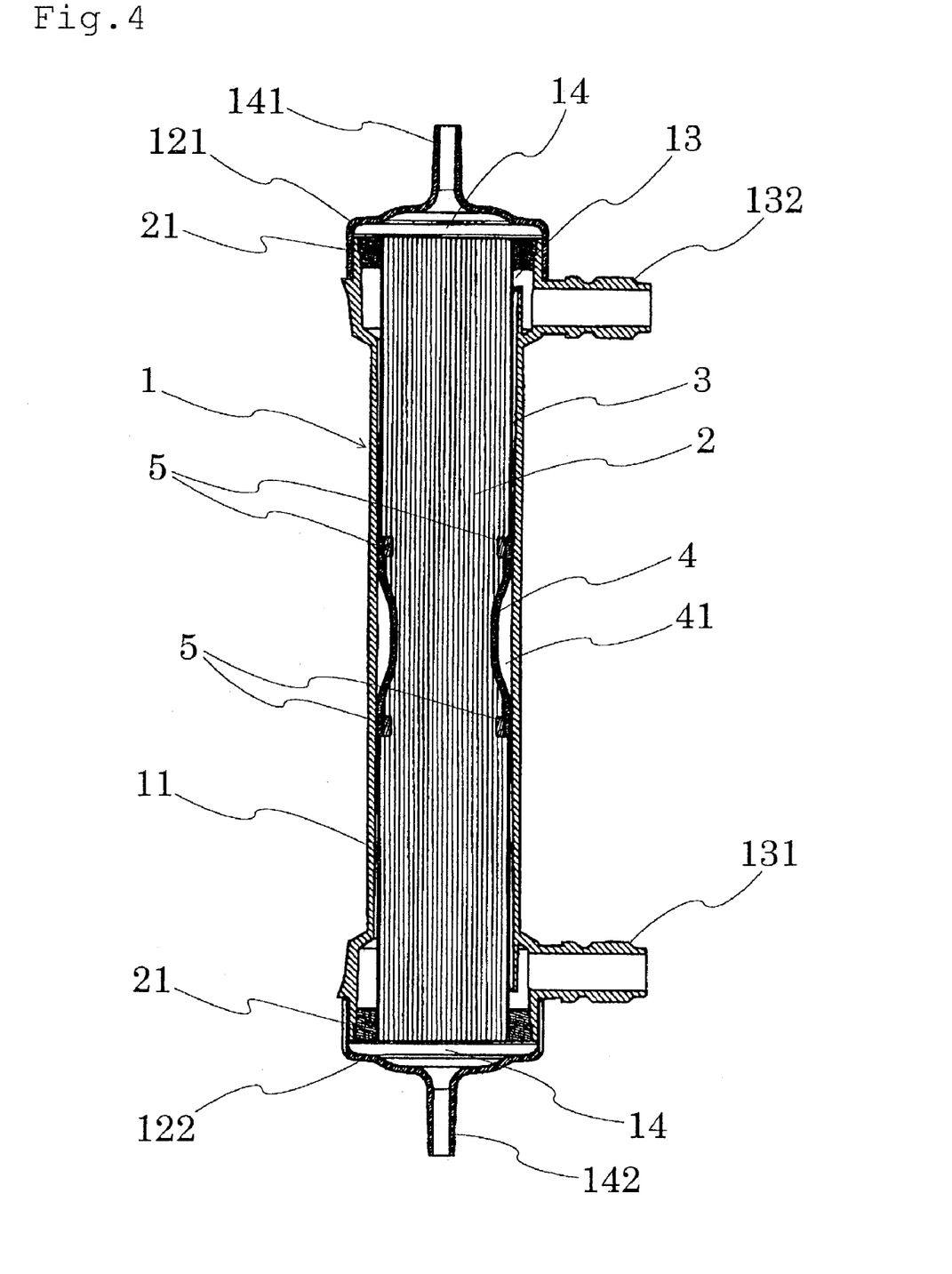
FIG. 4 is a longitudinal sectional view showing another embodiment of the dialyzer of the present invention.

When the heating of the heat-shrinkable tube 4 is conducted not locally but wholly, it is preferable that both ends of the heat-shrinkable tube 4 are fixed on the inner wall of the case body 11 as shown in FIG. 2. As shown in FIG. 4, it is more preferable to provide rings 5 mounted inside both ends of the heat-shrinkable tube 4 to liquid-tightly fix both ends of the tube 4 on the inner wall of the case body 11 so as not to communicate the space 41 with the dialyzate flow path 13. An outer diameter of the ring 5 is such a size that the ring 5 is liquid-tightly contacted with the inner wall of the heat-shrinkable tube 4. Further, the ring 5 preferably has such an inner diameter that the packing ratio of the hollow fiber bundle 3 in the portion in which the ring 5 is inserted is from 45 to 55%. When the ring 5 has an inner diameter that causes the packing ratio to be less than 45%, the ring 5 becomes a barrier when inserting the hollow fiber bundle 3 into the case 1, which may cause the hollow fiber membranes 2 to rupture.

The ring 5 is preferably made of a non-heat-shrinkable material such as polycarbonate or acrylic resin for enabling both ends of the heat-shrinkable tube 4 to be securely fixed on the inner wall of the case body 11.

Figure 5:
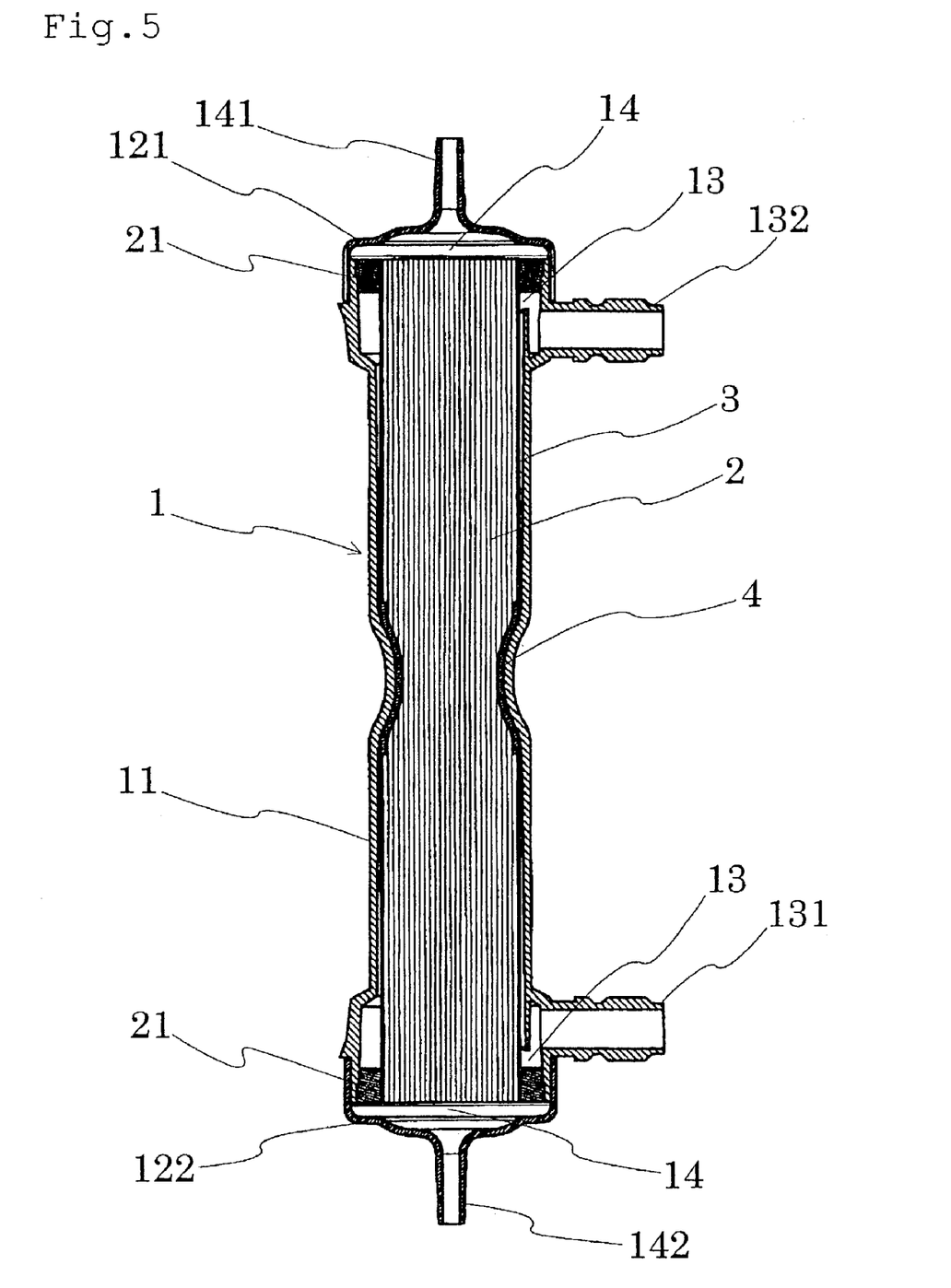
FIG. 5 is a longitudinal sectional view showing another embodiment of the dialyzer of the present invention.

The dialyzer in which the heat-shrinkable tube 4 is fixed to the inner wall of the case 1 shown in FIG. 2 may be one in which a part of the case body 11 which is close to the heat-shrinkable tube 4 is made of a heat-deformable material and is deformed to abut on the heat-shrinkable tube 4, as shown in FIG. 5, for eliminating the space 41 between the inner wall of the case body 11 and the heat-shrinkable tube 4. The whole of the case body 11 may be made of a heat-deformable material, for example, a thermoplastic material such as polycarbonate or polystyrene, or only a part close to the heat-shrinkable tube 4 in the case body 11 may be made of such a material.

The case body 11 may be deformed in a shape according to the shape of the heat-shrinkable tube 4 for eliminating the space 41 by heating with a heating device made of brass, or heating by infrared irradiation and compressing using a device made of brass as with the heat-shrinkable tube 4.

When the dialyzer of the present invention has the structure shown in FIG. 3 or 4, the sectional area of the dialyzate flow path 13 can be decreased by conducting the heating of the heat-shrinkable tube 4 not only locally but also wholly.

Figure 6:
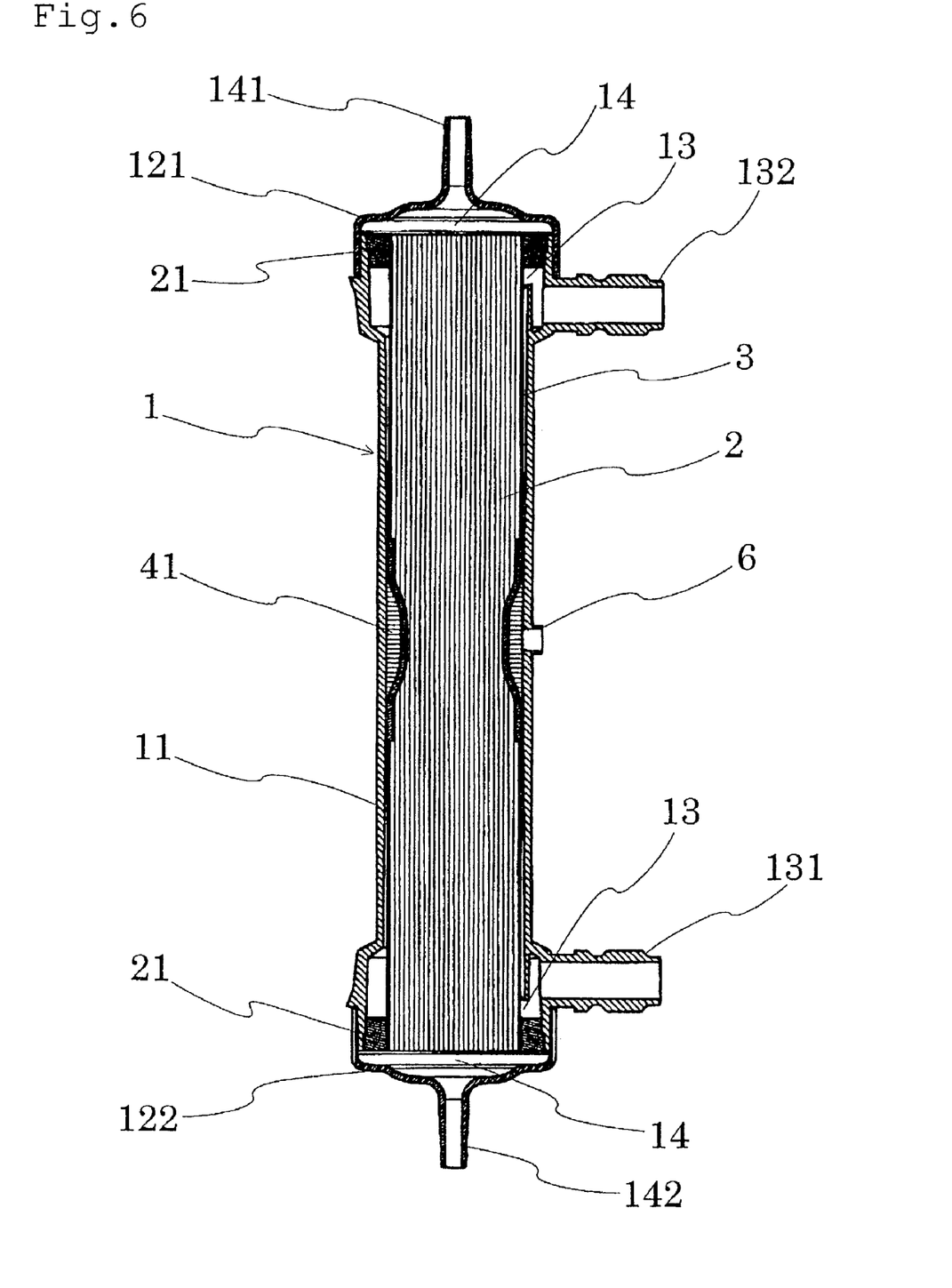
FIG. 6 is a longitudinal sectional view showing another embodiment of the dialyzer of the present invention.

Further, another example of the dialyzer of the present invention is that, as shown in FIG. 6, in which a filler is introduced into the space 41 between the inner wall of the case body 11 and the heat-shrinkable tube 4. The filler is introduced from, for example, a filler injection port 6 formed on the case body 11. As the filler, polyurethane, urethane foam, flowable heat-curing resin such as epoxy resin, a room temperature-curing silicon filler (RTV) or the like is preferably used.

Figures 7A, 7B, 7C:
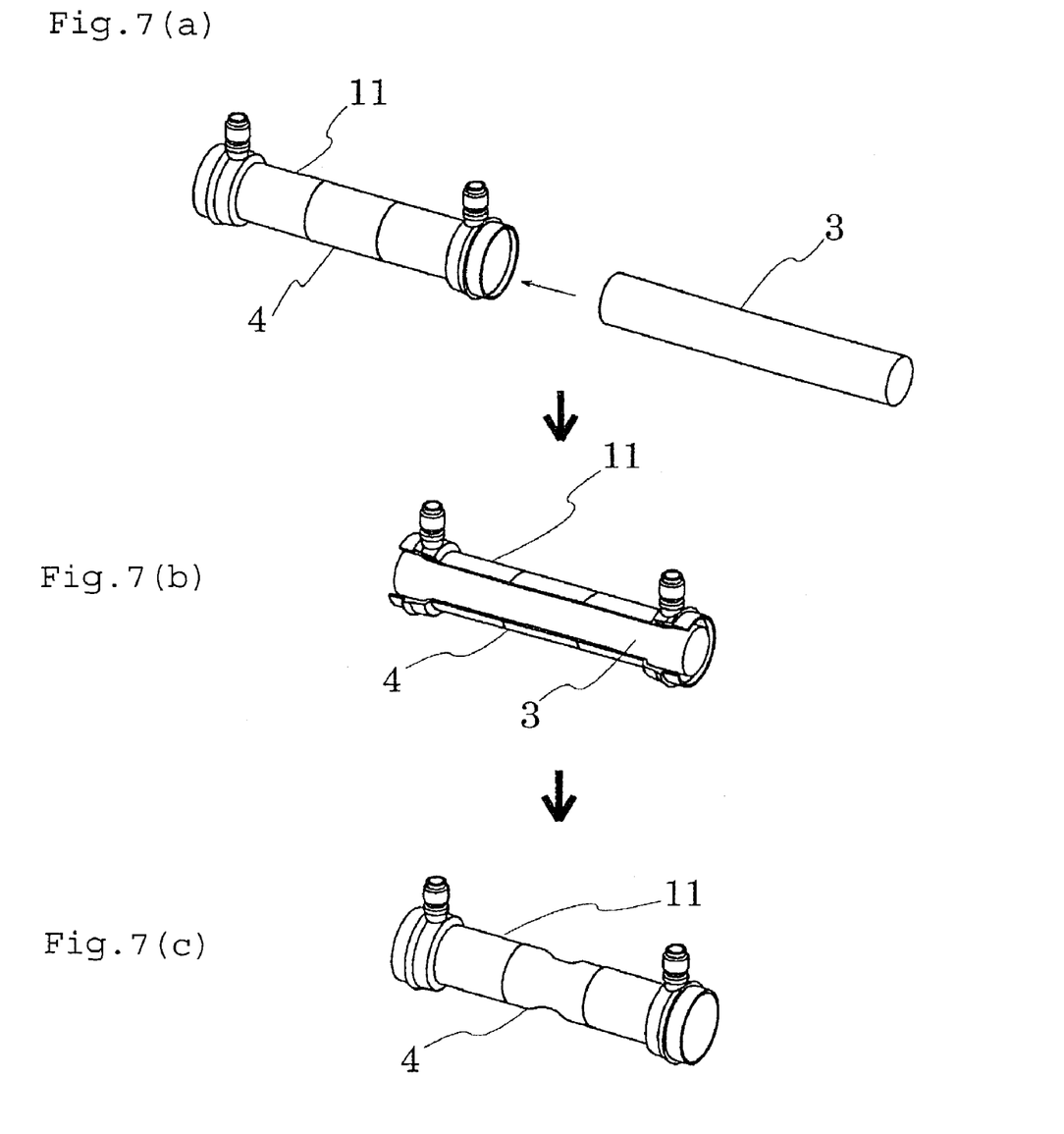

A method for manufacturing a dialyzer in which a part of the case body 11 is formed of the heat-shrinkable tube 4 as shown in FIG. 1 is illustrated in FIG. 7. The method for manufacturing the dialyzer as illustrated in FIG. 7 comprises the following steps (1) and (2).

(1) The hollow fiber bundle 3 is inserted in the lumen of the case body 11, a part of which is formed of the heat-shrinkable tube 4 (*a*).

(2) A potting agent is injected into both ends of the case body 11 in which the hollow fiber bundle 3 is inserted and obtained in the step (1) (*b*) to fix the hollow fiber bundle 3 within the case body 11, and at least a part of the heat-shrinkable tube 4 is then shrunk by heating (*c*).

After the steps (1) and (2), the caps 121 and 122 are mounted on both ends of the case body 11 to complete the manufacture of the dialyzer.

Figures 8A, 8B, 8C, 8D:
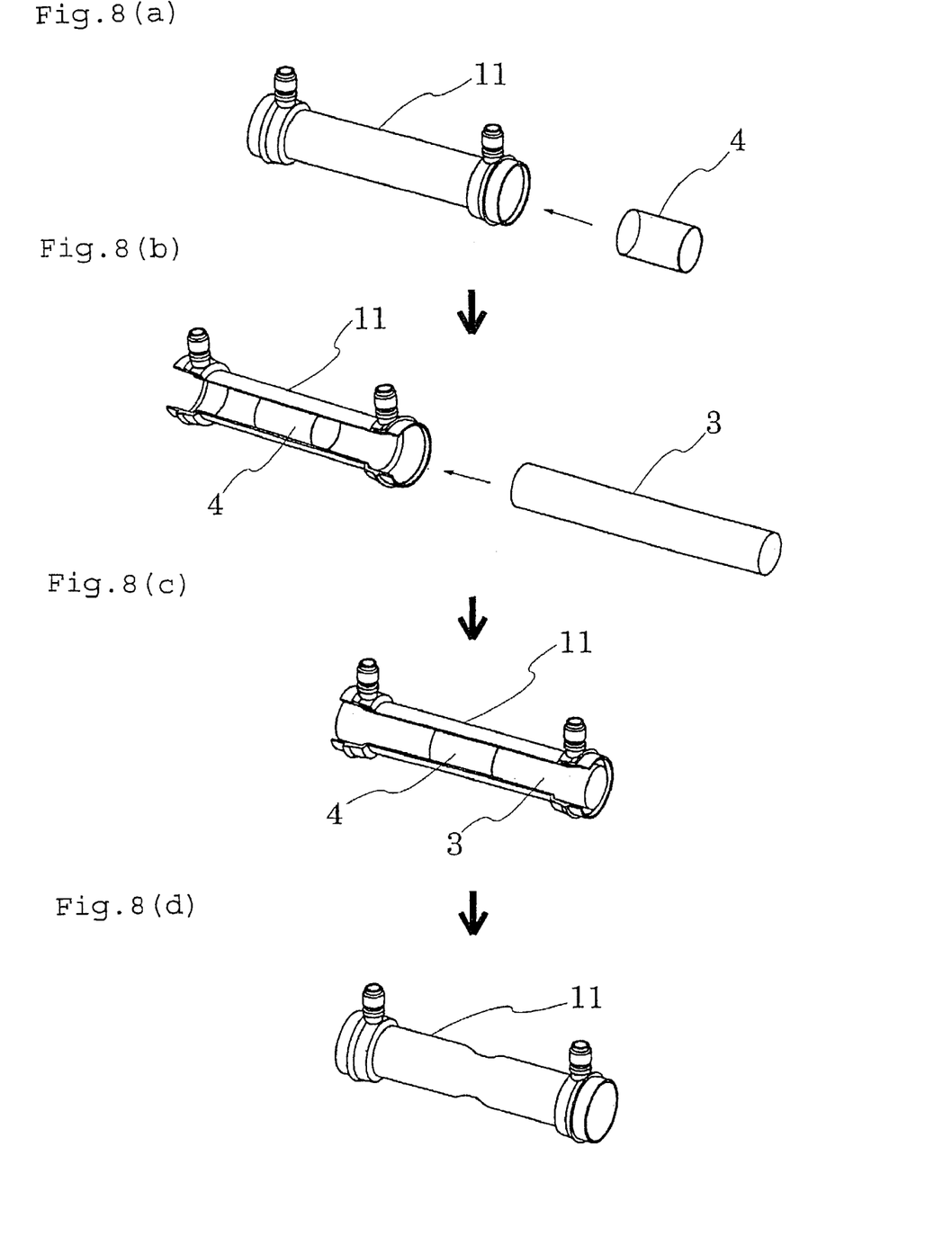

A method for manufacturing the dialyzer in which the heat-shrinkable tube 4 is fixed on the inner wall of the case 1 as shown in FIG. 5 is illustrated in FIG. 8. The method for manufacturing the dialyzer as illustrated in FIG. 8 comprises the following steps (1) to (3).

(1) First, the heat-shrinkable tube 4 which is not shrunk is inserted in the vicinity of the central portion of the case body 11 (*a*).

(2) Subsequently to the step (1), the hollow fiber bundle 3 is inserted into the lumen of the heat-shrinkable tube 4 within the case body 11 (*b*).

(3) A potting agent is injected into both ends of the case body 11 obtained in step (2) in which the heat-shrinkable tube 4 and the hollow fiber bundle 3 are inserted (*c*) to fix the hollow fiber bundle 3 within the case body 11, and at least a part of the heat-shrinkable tube 4 is then shrunk by heating (*d*).

In the example shown in FIG. 8, the part of the case body 11 which is close to the heat-shrinkable tube 4 is also heated simultaneously, and deformed to abut on the heat-shrinkable tube 4. After the steps (1) to (3), the caps 121 and 122 are mounted on both ends of the case body 11 to complete the manufacture of the dialyzer.

In a conventional method for manufacturing a dialyzer using a cylindrical product having a property of being swelled with a dialyzate, a hollow fiber bundle is inserted into a lumen of the product which has a far smaller inner diameter than an inner diameter of a case, and the product is then inserted into the case along with the hollow fiber bundle. The insertion of the hollow fiber bundle into the lumen of the product in such a dialyzer is quite difficult, and there is also a likelihood of rupturing the hollow fiber membranes. However, in the method for manufacturing the dialyzer in the present invention, the heat-shrinkable tube 4 having a large inner diameter and which is not shrunk is previously inserted into the case body 11. Accordingly, the insertion of the heat-shrinkable tube 4 into the case body 11 is easy and the insertion of the hollow fiber bundle 3 into the case 1 is conducted without difficulty by using a conventional device as such.

Figure 9:
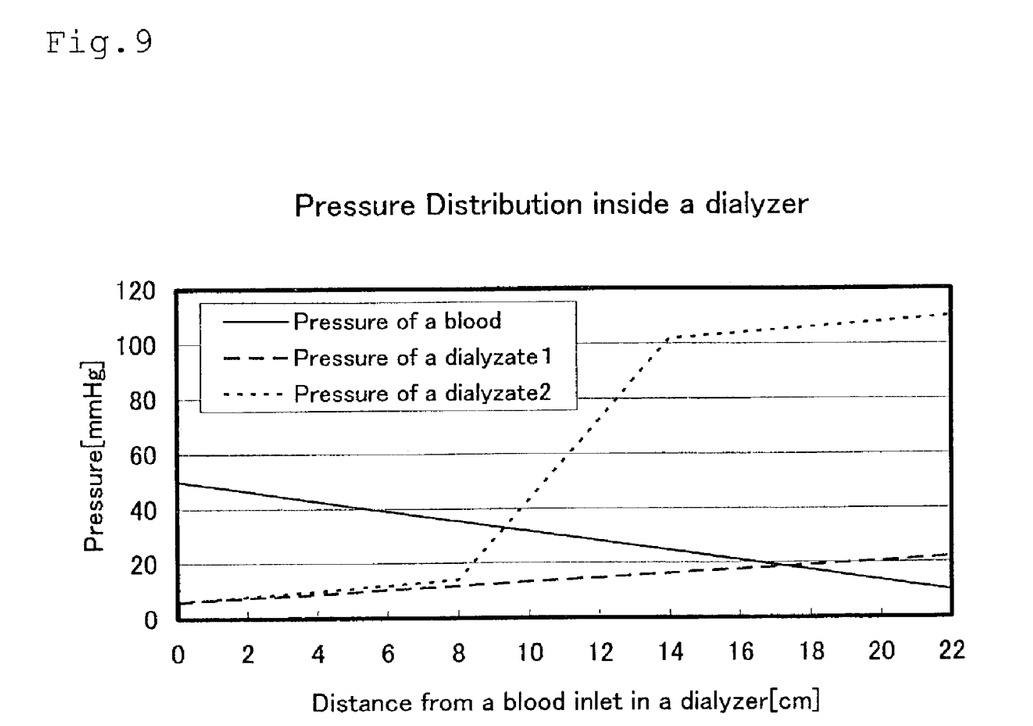
FIG. 9 is a graph of pressure distribution inside a dialyzer as a function of distance from blood inlet.

FIG. 9 is a graph showing pressure distribution of a fluid in the blood flow path 14 and the dialyzate flow path 13 in the dialyzer when the blood and the dialyzate flow in the dialyzer of the present invention.

The internal filtration and the internal backfiltration of the dialyzer occur by a difference between the pressure of the blood in the blood flow path 14 and the pressure of the dialyzate in the dialyzate flow path 13 (transmembrane pressure difference TMP). As shown by a line of the pressure of the blood and a line of the pressure of the dialyzate 1 in the graph, the internal filtration occurs in the vicinity of the blood inlet 141 (left side in the graph) because the pressure of the blood in the blood flow path 14 is higher than the pressure of the dialyzate in the dialyzate flow path 13. Internal backfiltration occurs in the vicinity of the blood outlet 142 (right side in the graph) because the pressure of the blood in the blood flow path 14 is lower than the pressure of the dialyzate in the dialyzate flow path 13. As TMP is greater, the internal filtration and the internal backfiltration of a large amount of fluid occur. The difference between the internal backfiltration rate and the internal filtration rate (internal backfiltration rate minus internal filtration rate) corresponds to a dewatering rate. The dewatering rate is controlled for each patient who undergoes dialysis by a dewatering rate controller incorporated in a general equipment for dialysis.

In the dialyzer of the present invention, the heat-shrinkable tube 4 is used for increasing TMP. When the heat-shrinkable tube 4 is shrunk by heating, the sectional area of the dialyzate flow path 13 is decreased as shown in FIGS. 1 to 6. As a result of the decrease in the sectional area of the dialyzate flow path 13, the pressure of the dialyzate is abruptly increased at the portion in which the heat-shrinkable tube 4 is inserted as shown by the line of the pressure of the dialyzate 2 in the graph. As a result, TMP is increased to allow the internal filtration and the internal backfiltration of a large amount of fluid.

EXAMPLES OF THE INVENTION

Examples that specifically illustrate the invention are described below.

Example 1

A tube made of polytetrafluoroethylene (hereinafter abbreviated as PTFE) and having a total length of 60 mm and an outer diameter of 36 mm was inserted into a central portion of a case body of a dialyzer made of polycarbonate and having a total length of 272 mm and an inner diameter of 36.5 mm. Subsequently, a hollow fiber bundle obtained by bundling approximately 9,000 hollow fiber membranes each made of polyether sulfone and having an inner diameter of 200 μm and an outer diameter of 260 μm was inserted into the lumen of the tube. A potting agent was injected into both ends of the case body to fix the hollow fiber bundle in the case body. An effective membrane area of the hollow fiber bundle was 1.5 m², and a packing ratio of the hollow fiber bundle was 45%. Then, the case body in the dialyzer was heated at 100° C. with a heater from an outer surface of the case body to locally heat and shrink the central portion of the PTFE tube, and caps were then mounted on both ends of the case body to manufacture a dialyzer. In the dialyzer, an inner diameter of the shrunk portion of the heat-shrinkable tube was 28.5 mm, a length of the shrunk portion of the heat-shrinkable tube was 40 mm, and the packing ratio of the hollow fiber bundle in the shrunk portion was 77%.

Example 2

A PTFE tube having a total length of 60 mm and an outer diameter of 36 mm was inserted into a central portion of a case is body of a dialyzer made of polycarbonate and having a total length of 272 mm and an inner diameter of 36.5 mm. Further, rings each having a cross-section which is a trapezium made of polycarbonate and having an inner diameter of 34.0 mm, an outer diameter of 35.5 mm at a distal end and an outer diameter of 36.5 mm at a proximal end were inserted into both ends of the lumen of the tube to fix the tube in the case body. Subsequently, a hollow fiber bundle obtained by bundling approximately 9,000 hollow fiber membranes each made of polyether sulfone and having an inner diameter of 200 μm and an outer diameter of 260 μm was inserted into the lumen of the tube. A potting agent was injected into both ends of the case body to fix the hollow fiber bundle in the case body. An effective membrane area of the hollow fiber bundle was 1.5 m², and a packing ratio of the hollow fiber bundle was 45%. Then, the case body in the dialyzer was heated at 100° C. with a heater from an outer surface of the case body to locally heat and shrink the central portion of the PTFE tube. Moreover, the case body was deformed to abut on the tube by being heated with a heater, and caps were then mounted on both ends of the case body to manufacture a dialyzer. In the dialyzer, an inner diameter of the shrunk portion of the heat-shrinkable tube was 28.5 mm, a length of the shrunk portion of the heat-shrinkable tube was 40 mm, and the packing ratio of the hollow fiber bundle in the shrunk portion was 77%.

Example 3

A PTFE tube having a total length of 60 mm and an outer diameter of 36 mm was inserted into a central portion of a case body of a dialyzer made of polycarbonate and having a total length of 272 mm and an inner diameter of 36.5 mm. Subsequently, a hollow fiber bundle obtained by bundling approximately 9,000 hollow fiber membranes each made of polyether sulfone and having an inner diameter of 200 μm and an outer diameter of 260 μm was inserted into the lumen of the tube. A potting agent was injected into both ends of the case body to fix the hollow fiber bundle in the case body. An effective membrane area of the hollow fiber bundle was 1.5 m², and a packing ratio of the hollow fiber bundle was 45%. Then, the case body in the dialyzer was heated at 100° C. with a heater from an outer surface of the case body to locally heat and shrink the central portion of the PTFE tube. Moreover, the case body was deformed to abut on the tube by being heated with a heater, and caps were then mounted on both ends of the case body to manufacture a dialyzer. In the dialyzer, an inner diameter of the shrunk portion of the heat-shrinkable tube was 28.5 mm, a length of the shrunk portion of the heat-shrinkable tube was 60 mm, and the packing ratio of the hollow fiber bundle in the shrunk portion was 77%.

Example 4

A PTFE tube having a total length of 60 mm and an outer diameter of 36 mm was inserted into a central portion of a case body of a dialyzer made of polycarbonate and having a total length of 272 mm and an inner diameter of 36.5 mm. Subsequently, a hollow fiber bundle obtained by bundling approximately 9,000 hollow fiber membranes each made of polyether sulfone and having an inner diameter of 200 μm and an outer diameter of 260 μm was inserted into the lumen of the tube. A potting agent was injected into both ends of the case body to fix the hollow fiber bundle in the case body. An effective membrane area of the hollow fiber bundle was 1.5 m², and a packing ratio of the hollow fiber bundle was 45%. Then, the case body in the dialyzer was heated at 100° C. with a heater from an outer surface of the case body to locally heat and shrink the central portion of the PTFE tube. Moreover, urethane foam was charged into a space between the inner wall of the case body and the PTFE tube, and caps were then mounted on both ends of the case body to manufacture a dialyzer. In the dialyzer, an inner diameter of the shrunk portion of the heat-shrinkable tube was 28.5 mm, a length of the shrunk portion of the heat-shrinkable tube was 55 mm, and the packing ratio of the hollow fiber bundle in the shrunk portion was 77%.

Comparative Example 1

A hollow fiber bundle obtained by bundling approximately 9,000 hollow fiber membranes each made of polyether sulfone and having an inner diameter of 200 μm and an outer diameter of 260 μm was inserted into a lumen of a case body of a dialyzer made of polycarbonate and having a total length of 272 mm and an inner diameter of 36.5 mm. A potting agent was injected into both ends of the case body to fix the hollow fiber bundle in the case body. An effective membrane area of the hollow fiber bundle was 1.5 m², and a packing ratio of the hollow fiber bundle was 45%. Caps were then mounted on both ends of the case body to manufacture a dialyzer.

A dialyzate was passed through the dialyzate flow path of the dialyzer obtained in each of Examples 1 to 4 and Comparative Example 1 at a flow rate of 500 mL/min, and a pressure loss of the dialyzate was measured by measuring pressures of the dialyzate at the dialyzate inlet and the dialyzate outlet. The results are shown in Table 1.

Further, a dialysis experiment of myoglobin (molecular weight 17,000) was conducted using the dialyzer obtained in each of Examples 1 to 4 and Comparative Example 1 to measure clearance. The flow rate conditions in the measurement are that a blood flow rate is 200 mL/min, a dialyzate flow rate is 500 mL/min and a dewatering rate is 0 mL/min. The results are shown in Table 1.

TABLE 1

|  | Pressure loss [mmHg] | Clearance (mL/min) |
| --- | --- | --- |
| Example 1 | 70 | 78 |
| Example 2 | 90 | 80 |
| Example 3 | 120 | 82 |

TABLE 1-continued

| | Pressure loss [mmHg] | Clearance (mL/min) |
|---|---|---|
| Example 4 | 110 | 81 |
| Comparative Example 1 | 15 | 72 |

As shown in Table 1, it is found that the pressure loss of the dialyzate in the dialyzer of the present invention in Examples 1 to 4 is significantly increased in comparison to the pressure loss of the dialyzate in the conventional dialyzer in Comparative Example 1. It is further found that the clearance of myoglobin in the dialyzer of the present invention in Examples 1 to 4 is increased in comparison to the clearance in the conventional dialyzer in Comparative Example 1.

The results reveal that the dialyzer of the present invention which is provided with the heat-shrinkable tube is, in comparison to the conventional dialyzer not having the heat-shrinkable tube, decreased in the sectional area of the dialyzate flow path to thereby clearly increase the internal filtration rate and the internal backfiltration rate.

EFFECT OF THE INVENTION

The dialyzer of the present invention can increase the flux of internal filtration and the flux of internal backfiltration by providing a cylindrical heat-shrinkable tube at least a part of which is shrunk by heating. Further, since the sectional area of the dialyzate flow path is sufficiently decreased by shrinking the heat-shrinkable tube through heating, the flux of internal filtration and the flux of internal backfiltration can easily be increased. Moreover, in the method for manufacturing the dialyzer of the present invention, the heat-shrinkable tube is previously inserted in the case of the dialyzer and the hollow fiber bundle is then inserted. Accordingly, the dialyzer can easily be manufactured without using a special device and without fear of rupturing the hollow fiber membranes.

What is claimed is:

1. A method for manufacturing a dialyzer comprising a substantially cylindrical case, a hollow fiber bundle made of a plurality of hollow fiber membranes provided in said case, a blood flow path formed by lumens of the hollow fiber membranes, a dialyzate flow path formed by gaps between the hollow fiber membranes and between the inner wall of the case and the hollow fiber membranes and a cylindrical heat-shrinkable tube provided on an outside of the hollow fiber bundle wherein at least a part of said heat-shrinkable tube can be shrunk by heating and wherein the heat-shrinkable tube is fixed to the inner wall of the case with rings inserted in the lumen of the heat-shrinkable tube, comprising the following steps (1) to (3), (1) inserting the cylindrical heat-shrinkable tube into the substantially cylindrical case,
   (2) subsequently, inserting the hollow fiber bundle into a lumen of the heat-shrinkable tube in the case, and
   (3) subsequent to step (2), heating at least a part of the heat-shrinkable tube in the case to shrink the tube.

2. A method for manufacturing a dialyzer comprising substantially cylindrical case, a hollow fiber bundle made of a plurality of hollow fiber membranes provided in said case, a blood flow path formed by lumens of the hollow fiber membranes, a dialyzate flow path formed by gaps between the hollow fiber membranes and between the inner wall of the case and the hollow fiber membranes and a cylindrical heat-shrinkable tube provided on an outside of the hollow fiber bundle wherein at least a part of said heat-shrinkable tube can be shrunk by heating and wherein at least a part of said case close to the heat-shrinkable tube is formed of a heat-deformable material, and can be deformed together with the heat-shrinkable tube, comprising the following steps (1) to (3), (1) inserting the cylindrical heat-shrinkable tube into the substantially cylindrical case,
   (2) subsequently, inserting the hollow fiber bundle into a lumen of the heat-shrinkable tube in the case, and
   (3) subsequent to step (2), heating at least a part of the heat-shrinkable tube and substantially cylindrical case to shrink the tube and said at least a part of said case.

3. A method for manufacturing a dialyzer comprising a substantially cylindrical case, a hollow fiber bundle made of a plurality of hollow fiber membranes provided in said case, a blood flow path formed by lumens of the hollow fiber membranes, a dialyzate flow path formed by gaps between the hollow fiber membranes and between the inner wall of the case and the hollow fiber membranes and a cylindrical heat-shrinkable tube provided on an outside of the hollow fiber bundle wherein at least a part of said heat-shrinkable tube can be shrunk by heating and wherein the case has a filler injection port to introduce a filler into a space between the inner wall of the case and the heat-shrinkable tube after shrinking, comprising the following steps (1) to (4), (1) providing the substantiall clindrical case having the filler injection port provided therein,
   (2) inserting the cylindrical heat-shrinkable tube into the substantially cylindrical case,
   (3) subsequently, inserting the hollow fiber bundle into a lumen of the heat-shrinkable tube in the case, and
   (4) subsequent to step (3), heating at least a part of the heat-shrinkable tube in the case to shrink the tube.

* * * * *